United States Patent
Fitzgerald (10) Patent No.: US 12,397,218 B2
(45) Date of Patent: Aug. 26, 2025

(54) METHOD AND SYSTEM FOR DETERMINING GOLF HANDICAP AS A FUNCTION OF BLOOD ALCOHOL CONCENTRATION

(71) Applicant: Paul Fitzgerald, Hillsborough, NJ (US)

(72) Inventor: Paul Fitzgerald, Hillsborough, NJ (US)

(73) Assignee: Paul Fitzgerald, Hillsborough, NJ (US)

( * ) Notice: Subject to any disclaimer, the term of this patent is extended or adjusted under 35 U.S.C. 154(b) by 279 days.

(21) Appl. No.: 18/201,340

(22) Filed: May 24, 2023

(65) Prior Publication Data

US 2024/0390764 A1 Nov. 28, 2024

(51) Int. Cl.
*A63B 71/06* (2006.01)

(52) U.S. Cl.
CPC .......... *A63B 71/06* (2013.01); *A63B 2220/12* (2013.01); *A63B 2225/20* (2013.01); *A63B 2225/50* (2013.01); *A63B 2230/20* (2013.01)

(58) Field of Classification Search
CPC ............... A63B 71/06; A63B 2220/12; A63B 2225/20; A63B 2225/50; A63B 2230/20; A63B 67/02; G16H 20/30
See application file for complete search history.

(56) References Cited

U.S. PATENT DOCUMENTS

| | | | |
|---|---|---|---|
| 10,390,732 B2 * | 8/2019 | Ross | A61B 90/90 |
| 2009/0292178 A1 * | 11/2009 | Ellis | G16H 10/60 |
| | | | 600/301 |
| 2018/0093182 A1 * | 4/2018 | Healey | A63F 13/92 |

* cited by examiner

*Primary Examiner* — Ronald Laneau (57) ABSTRACT

Provided are computer server-implemented methods for adjusting handicaps of players playing golf based on their level of intoxication. Such methods includes steps of (a) receiving handicap information of at least one player over a data network; and a step (b) receiving over the data network information associated with a golf course that the at least one player will play, the golf course information including levels of difficulty of playing respective holes of a plurality of holes of the golf course over the data network. These methods may also include a step of transmitting to the user device the BAC handicap for each player for the hole to be played, wherein the BAC handicap includes an indication of any award of extra strokes to one of the players for a hole to be played based on both such player's skill level and level of intoxication.

10 Claims, 6 Drawing Sheets

| Golfer BAC | BAC Hole Stroke factor |
|---|---|
| 0 - .01 | 0 |
| .011 - .02 | 0.08 |
| .021 - .03 | 0.16 |
| .031 - .04 | 0.24 |
| .041 - .05 | 0.32 |
| .051 - .06 | 0.4 |
| .061 - .07 | 0.48 |
| .071 - .08 | 0.56 |
| .081 - .09 | 0.64 |
| .091 - .10 | 0.72 |
| .101 - .11 | 0.8 |
| .111 - .12 | 0.88 |
| .121 - .13 | 0.96 |
| .131 - .14 | 1.04 |
| .141 - .15 | 1.12 |
| .151 - .16 | 1.2 |
| .161 - .17 | 1.28 |
| .171 - .18 | 1.36 |
| .181 - .19 | 1.44 |
| .191 - .20 | 1.52 |
| .201 - .21 | 1.64 |
| .211 - .22 | 1.76 |
| .221 - .23 | 1.88 |
| .231 - .24 | 2 |
| .241 - .25 | 2.12 |

| Hole Difficulty Index (HDI) | |
|---|---|
| GCHH | |
| 1 | 0.5 |
| 2 | 0.47222 |
| 3 | 0.44444 |
| 4 | 0.41666 |
| 5 | 0.38888 |
| 6 | 0.3611 |
| 7 | 0.33332 |
| 8 | 0.30554 |
| 9 | 0.27776 |
| 10 | 0.24998 |
| 11 | 0.2222 |
| 12 | 0.19442 |
| 13 | 0.16664 |
| 14 | 0.13886 |
| 15 | 0.11108 |
| 16 | 0.0833 |
| 17 | 0.05552 |
| 18 | 0.02774 |

FIG. 6

| | Hole | Golf Course Hole Handicap GCHH | Standard Handicap Stroke per hole SHS | Hole Difficulty Index # HDI | BAC on each hole BAC | Hole BAC Calculation (HDI + BAC) | (Integer value) Bac Index plus HDI strokes per hole =INT(P8+M8) |
|---|---|---|---|---|---|---|---|
| | 1 | 6 | 1 | 0.3611 | 0 | 0.3611 | 1 |
| | 2 | 3 | 1 | 0.44444 | 0.021 | 0.60444 | 1 |
| | 3 | 16 | | 0.0833 | 0.03 | 0.2433 | 0 |
| | 4 | 9 | 1 | 0.41666 | 0.032 | 0.65666 | 1 |
| | 5 | 12 | | 0.19442 | 0.02 | 0.27442 | 0 |
| | 6 | 17 | | 0.05552 | 0.04 | 0.29552 | 0 |
| | 7 | 8 | 1 | 0.30554 | 0.044 | 0.62554 | 1 |
| | 8 | 5 | 1 | 0.38888 | 0.06 | 0.78888 | 1 |
| | 9 | 2 | 1 | 0.47222 | 0.12 | 1.35222 | 2 |
| | 10 | 11 | | 0.2222 | 0.151 | 1.4222 | 1 |
| | 11 | 14 | | 0.13886 | 0.142 | 1.25886 | 1 |
| | 12 | 15 | | 0.11108 | 0.123 | 1.07108 | 1 |
| | 13 | 18 | | 0.02774 | 0.162 | 1.30774 | 1 |
| | 14 | 7 | 1 | 0.33332 | 0.111 | 1.21332 | 2 |
| | 15 | 4 | 1 | 0.41666 | 0.094 | 1.13666 | 2 |
| | 16 | 1 | 1 | 0.5 | 0.088 | 1.14 | 2 |
| | 17 | 10 | | 0.24998 | 0.05 | 0.56998 | 0 |
| | 18 | 13 | | 0.16664 | 0.082 | 0.80664 | 0 |

Example calculation
Golfer's Handicap Index 9.4
Course A, White Tees

Regular HI total strokes    9                BAC included Total Stroke    17

METHOD AND SYSTEM FOR DETERMINING GOLF HANDICAP AS A FUNCTION OF BLOOD ALCOHOL CONCENTRATION

FIELD OF THE INVENTION

The invention generally relates to golf, and more particularly, to golf handicap systems and methods for determining a golf handicap as a function of blood alcohol concentration.

BACKGROUND OF THE INVENTION

Golf is a club-and-ball sport in which players use various clubs to hit balls into a series of holes on a course in as few strokes as possible. Golf is extremely popular, according to data from the National Golf Foundation 25.1 million people played on a golf course in the United States in 2021.

Golf, unlike most ball games, does not use a standardized playing area, and coping with the varied terrains encountered on different courses is a key part of the game. Golf courses typically have either 18 or 9 holes located within respective regions of terrain of a golf course, wherein each hole is the target for receiving the ball during play. Each hole on a course contains a teeing ground to start from, and a putting green containing the cup for the hole. The idea of golf is to get the ball in each of the holes in the fewest strokes possible. The golfer tees off for each hole with the aim of getting the ball as close as possible to the putting green—or as close to the hole as possible, and then take subsequent strokes to hit the ball into the hole.

Each of the holes of a golf course has an established difficulty level from lowest to highest, expressed as the hole's handicap, and a predetermined number of strokes called "par," which an expert golfer would be expected to take to hit the ball into the hole starting from the teeing ground. An individual golfer can establish a handicap by submitting 20 golf scores to a regulating body, which uses a complex algorithm to determine an individual golfer's handicap. The purpose of this handicap is to allow golfers of various abilities to compete effectively and fairly against each other in a round of golf. This is accomplished by awarding extra strokes above the par value to the lesser-skilled golfers on the more difficult holes of a golf course based on the difference in the handicaps (or skill levels) amongst the players.

Many golfers consumer alcohol while playing golf. Consuming alcohol is associated temporary impairments including, for example, dulling of senses, loss of coordination, loss of focus, and/or erratic behavior. The severity of these alcohol impairments increase with increased alcohol consumption. Such impairments may occur shortly after alcohol consumption and continue for several hours before tapering off. However, traditional golf handicaps do not take into consideration the amount of alcohol consumed by the golfer or the blood alcohol content of the golfer.

SUMMARY OF THE INVENTION

Provided are methods and systems for determining a further adjustment to an individual player's handicap based on the player's detected or estimated blood alcohol concentration ("BAC") prior to playing one or more holes during a round of golf.

Such methods and systems advantageously implement an additional factor to the golf handicapping system by introducing an additional factor of the individual golfer's detected or estimated BAC for adjusting such golfer's golf handicap during a round of golf in which the golfer is consuming alcoholic beverages. As expected, an increase in a golfer's BAC level during play, decreases such golfer's ability to maintain precise eye hand coordination. Thus, a higher BAC will correspondingly increase any golfer's difficulty for playing. Because each golfer will have a different detected or estimated BAC based on the number of drinks consumed, the golfer's weight and other factors, each golfer will experience a corresponding level of intoxication and change in the level of difficulty playing golf at such time.

In one exemplary embodiment, a computer server-implemented method adjusts handicaps of players playing golf based on their level of intoxication. This computer server-implemented method includes (a) receiving handicap information of one or more players over a data network; (b) of receiving over the data network information associated with a golf course that at least one player will play, the golf course information including levels of difficulty of playing respective holes of a plurality of holes of the golf course over the data network; (c) determining player-hole indexes for each player based on the golf course information, the player handicap information for each player, and type of golf game to be played; (d) receiving player-hole information for each player over the data network from a user device associated with one or more of the players, the player-hole information including an identifier indicative of a hole to be played of the plurality of holes, and data concerning each player's BAC at such time, wherein the player BAC data is indicative of the BAC level of corresponding player immediately prior to that player playing the hole to be played; (e) for each player, determining a respective BAC handicap for the hole to be played based on such player's player-hole index for the hole to be played, and the received player BAC data; and (f) transmitting to the user device the BAC handicap for each player for the hole to be played, wherein the BAC handicap includes an indication of any award of extra strokes for each player for a hole to be played based on both such player's skill level and level of intoxication at such time.

The player's BAC data may be determined, for example, by at least one of information from a BAC detector, entry into the user device of the type and quantity of one or more alcoholic beverages consumed by the player, or other information provided by the player or user device. In certain embodiments, the BAC detector transmits detected player BAC information to the computer server via the user device. It is possible for such detector to utilize, for example, a conventional breathalyzer in wired or wireless (such as via the Bluetooth standard) communication with the user device, which may be, for example, a mobile device in the form of a mobile telephone, tablet or computer. In further embodiments of the computer server-implements method, the determining of the BAC handicap is based on at least one of an algorithm and a lookup table.

In certain embodiments, at least one of the received information associated with a golf course, and the received identifier indicative of a hole to be played is provided by the user device by, for example, selection or entry by a player, or based on global positioning system (GPS) information obtained by such user device.

BRIEF DESCRIPTION OF THE DRAWINGS

The drawings described below are for illustrative purposes only and are not intended to limit the scope of the invention.

DETAILED DESCRIPTION OF THE INVENTION

It is to be understood that the terminology employed herein is for the purpose of describing particular embodiments, and is not intended to be limiting. Further, although any methods, devices and materials similar or equivalent to those described herein can be used in the practice or testing of the invention, certain methods, devices and materials are now described.

Throughout this application, articles "a" and "an" are used in this disclosure to refer to one or more than one (i.e., to at least one) of the grammatical object of the article.

As used herein, "processor" means a microprocessor, microcontroller, gate array, discrete Boolean logic components, or any other single or group of components that would produce the desired output signals in accordance with the purge controller operation described and/or contemplated by this disclosure.

The disclosure is further illustrated by the following description, which are not to be construed as limiting this disclosure in scope or spirit to the specific procedures herein described. It is to be understood that the descriptions are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Golf is a game of skill with a relatively high level of difficulty. The vast majority of individuals playing golf do not score very well. It is well known that average players on a typical golf course having a "par" of 72, often achieve scores of total stokes hitting the ball into such golf course's holes considerably higher than that par value. GolfSpan.com, for example, has reported (at www.golfspan.com/percentage-golfers-break-100) that typical average score ranges by percentages of golfers for completing a round of golf on an 18 hole golf course is on the order of:

under 80 strokes-5% of golfers,
80-89 strokes-21% of golfers,
90-99 strokes-29% of golfers,
100-109 strokes-24% of golfers,
110-119 strokes-10% of golfers, and
over 120 strokes-11% of golfers.

Despite such high level of difficulty, the majority of golfer's consider golf a pleasurable game to be spent with friends. There are a large number of different types of golf games and variations thereof including, for example, such games known as Skins, Wolf, Rabbit, Vegas, Round Robin, "Bingo, Bango, Bongo." Frequently, alcoholic beverages are available and consumed by players while playing a round of golf. River's Edge Golf Course, for example, has been reported (at www.riversedgegolfbend.com/bend-oregon-golf-blog/demographics-of-golf) that approximately 22 percent of golfers enjoy one or two drinks while playing golf and 11 percent of golfers consume more than two alcoholic beverages while playing a round of golf.

The subject invention may be implemented using a remote internet-accessible computer server in communication with a user device associated with a player while playing golf, such as a mobile phone, tablet or computer, that receives data from a BAC detector, e.g., a breathalyzer, for measuring each golfer's BAC prior to the beginning of play, i.e., teeing off, for each hole (or one or more holes) of the golf course. Each player's measured BAC is then communicated in the form of BAC data to the computer server. The computer server uses the received BAC data for each player and the corresponding hole's playing difficulty (e.g., handicap, par, length, required carry distances, hazards) to establish a BAC-related hole handicap (or "BAC handicap") for each golfer. This BAC-related hole handicap can then be used by the players to "level the playing field" between players as their BAC varies between holes played and as their base skill level changes during the playing of the round of golf.

In certain embodiments, the method estimates or determines the BAC prior to the first golf shot at each hole. In embodiments within the subject method, the user device prompts the player to use a breathalyzer prior to taking the first golf shot at a hole or to input information indicative of an estimated BAC.

In certain embodiments, the user device may provide a warning alert to a player to pause consumption of alcohol at certain times when such consumption would cause the BAC results to be inaccurate at the time of a next tee off. For example, if the player's BAC is measured by a breathalyzer prior to hitting the golf ball from the tee box, then the user device with a global positioning system (GPS) may use the GPS location information as a basis for alerting the player to pause consuming alcohol when the user device detects a next tee box during the round of golf is within a certain distance, e.g., 5 to 20 yards, of the user device. Moreover, in some embodiments, the player may indicate to the user device that such player has been non-compliant with the warning, and the method would then not prompt the user for a new breathalyzer test, but instead use the BAC data provided from the breathalyzer value for the play of the previous hole.

Figure 1:
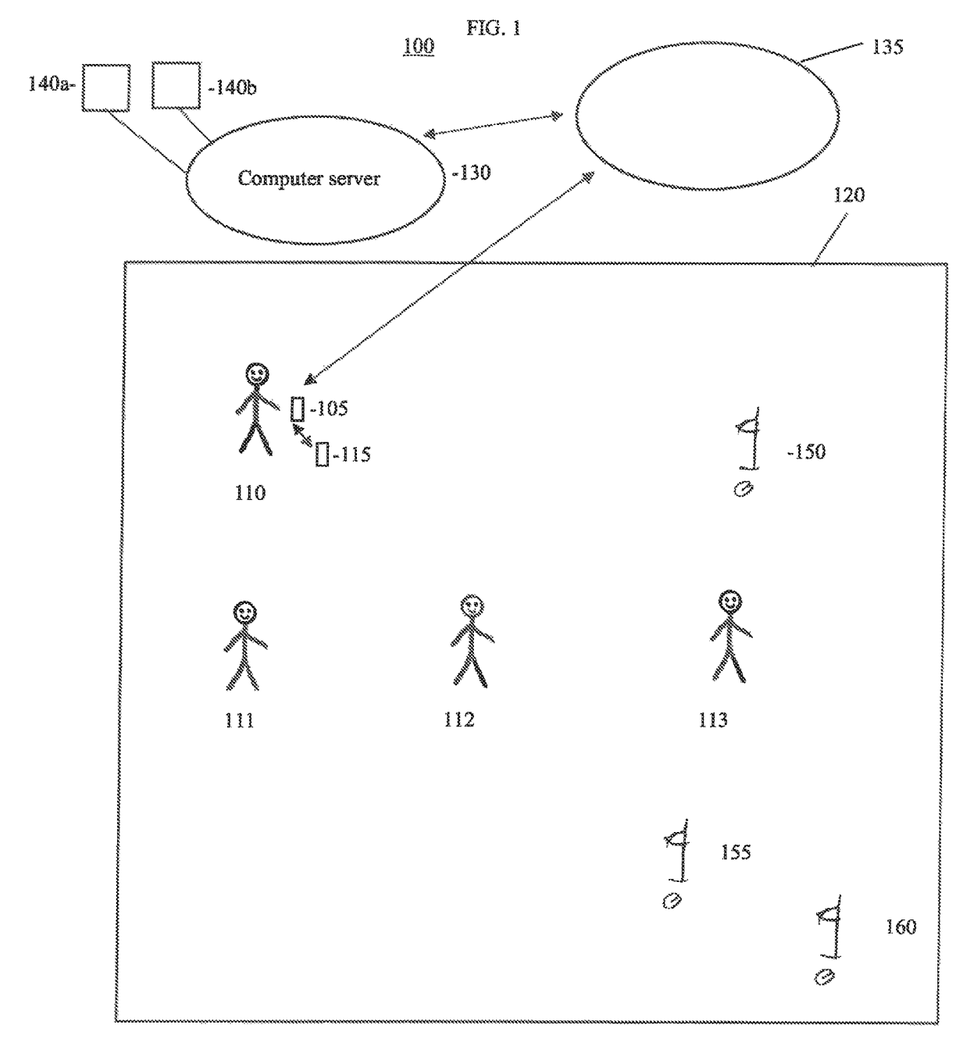
FIG. 1 depicts an exemplary schematic block diagrams of a representative system for implementing the methods of FIGS. 2 and 3.

FIG. 1 depicts a representative system 100 for implementing the methods of this disclosure during a round of golf. Referring to FIG. 1, four players 110, 111, 112, and 113 are depicted located on a golf course 120. The golf course 120 includes a number of holes, including at least holes 150, 155 and 160, for the playing of a round of golf by the players 110, 111, 112, and 113.

A user device 105 is accessible to at least one of the golfers, such as player 110. The user device 105 is configured for receiving player BAC data from a BAC detector 115, which may be a wired or wireless breathalyzer. Low cost Bluetooth-enabled breathalyzers are particularly suitable for the BAC detector 115.

The user device 105 may communicate with a remote internet-accessible computer server 130 to perform the process of determining the BAC-related hole handicap for each golfer, i.e., adjusting the respective handicaps of the players 110, 111, 112, and 113 based on their level of intoxication. The computer server 130 is further capable of communicating with one or more other representative internet-accessible computer servers 140*a* and 140*b*, which may be associated with the US Golf Association's Golf Handicap Information Network ("GHIN"), for providing golf course hole handicap information and/or individual golfer's handicap information. This communication occurs over data network 135, which may be or include the internet, and may be accessible by interconnected wired means, wireless means and combinations of wired and wireless means. It should be readily understood that the present invention is not limited to golf course hole handicap information and player handicap information from the GHIN, and that such handicap information may be obtained from any other source for use with the method of this disclosure.

As described further herein, when the players 110, 111, 112, and 113 are playing an exemplary round of golf on the golf course 120 and consuming alcohol, each of the players 110, 111, 112, and 113 may utilize the BAC detector 115 for measurement of their respective BAC for use by the computer server 130 in calculating the BAC-related hole handicap for each of the players 110, 111, 112, and 113.

It should be readily understood that the BAC detector 115 may be of a type to directly or indirectly through some other communication device communicate the BAC information of the players to the computer server 130. In the alternative, the BAC information of each player may be estimated by the user device 105, computer server 130, or some other device, based on the number of types of alcoholic beverages consumed by the player 110 with or without indicating the time period of which the beverages were consumed. In a further alternative, a player could enter other information into the user device 105 indicative of that players BAC level. For each player 110, 111, 112, and 113, the BAC data may include information in the typical form of indicating BAC of the percent of ethyl alcohol or ethanol in a player's blood stream, whereby a BAC of 0.1% means that an individual's blood supply contains one part alcohol for every 1000 parts blood.

Figure 2:
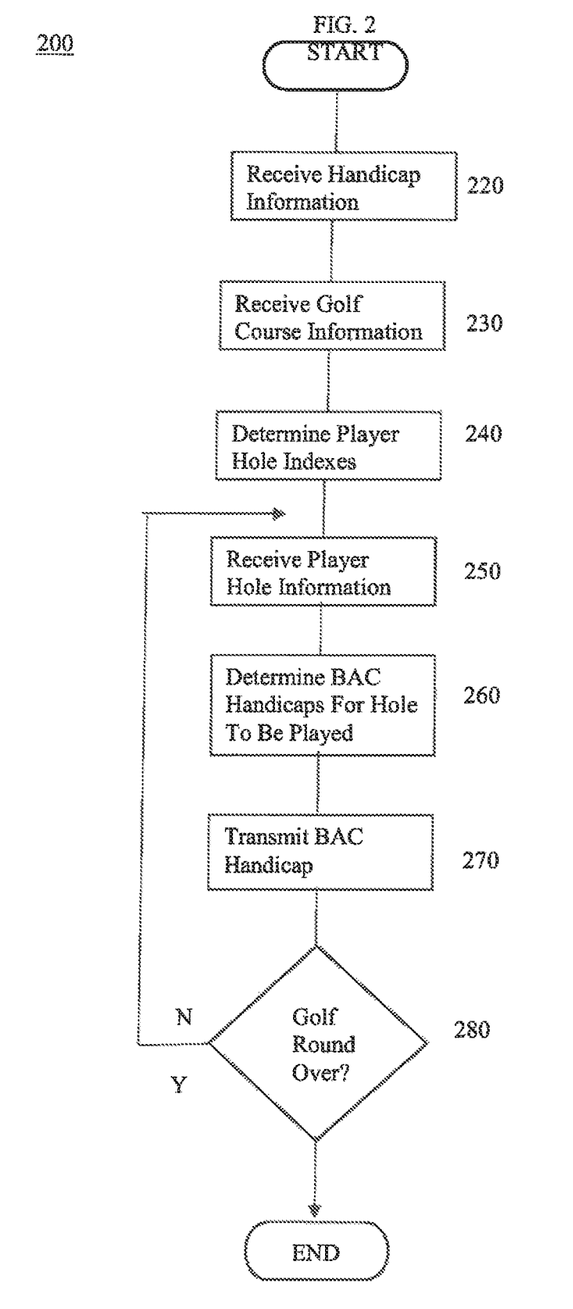
FIG. 2 depicts a flow diagram of an exemplary computer server-implemented method in accordance with this disclosure for adjusting handicaps of players playing golf based on their level of intoxication.
Figure 3:
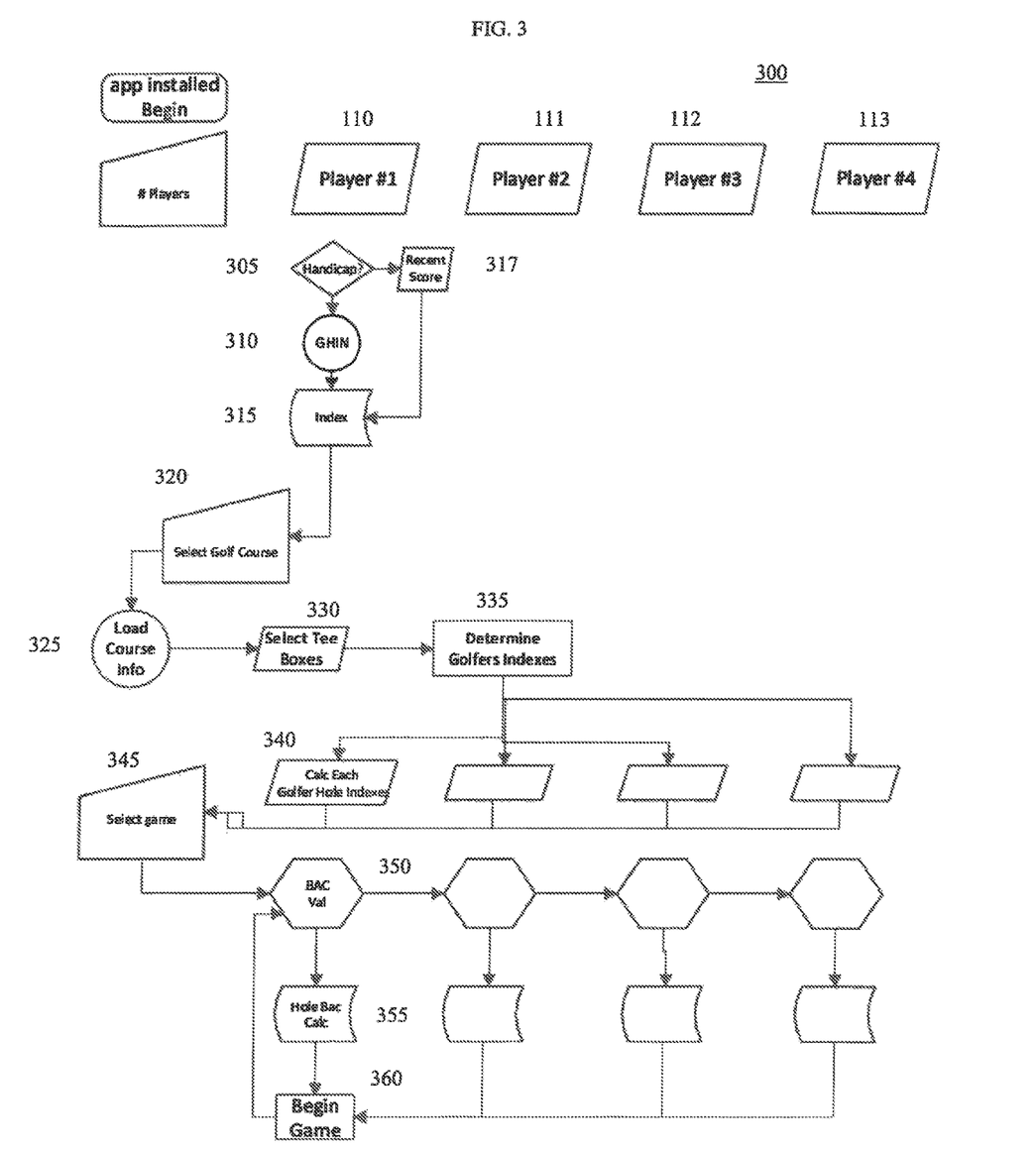
FIG. 3 depicts another flow diagram of an computer server-implemented method in accordance with this disclosure for adjusting handicaps of players playing golf based on their level of intoxication.

Further, it possible for more than one BAC detector and user device to be used during the round of golf for performing the methods of the disclosure including methods 200 and 300 illustrated in FIGS. 2 and 3.

FIG. 2 depicts a flow diagram of an exemplary method 200 that may be executed on the computer server 130 and system 100 of FIG. 1 for adjusting handicaps of golf players, such as players 110, 111, 112 and 113 of FIG. 1, playing golf based on their respective levels of intoxication at each hole, or particular holes, of a golf course. The method 200 begins at step 220, when the computer server 130 of FIG. 1 receives over data network 135 player handicap information for the players 110, 111, 112 and 113. In step 230, the computer server 130 receives over data network 135 information associated with the golf course 120 at which the players 110, 111, 112 and 113 will play.

Such golf course information may include, for example, indicators of the levels of difficulty of playing respective golf course holes (e.g. holes 150, 155 and 160). The player handicap information and golf course information may be received from the GHIN, i.e., computer servers 140*a* and/or 140*b*. In the alternative, the player handicap and golf course information may be received from other computer servers, computers or the user device 105.

Referring again to FIG. 2. After steps 220 and 230 are completed, the method 200 proceeds to step 240. In step 240, the player-hole indexes for players 110, 111, 112, and 113 are determined based on the golf course 120 information, the respective player's own handicap information and the type of golf game to be played. Then, in step 250, the player-hole information is received over the data network 135 from the user device 105 for each player 110, 111, 112, and/or 113.

The player-hole information includes an identifiers indicative of each hole (e.g. hole 150, 155, or 160) to be played on the golf course 120 and player BAC data, wherein the respective player BAC data is indicative of the blood alcohol concentration for each player 110, 111, 112, and 113 immediately prior to playing the hole to be played by the players.

Referring again to FIG. 2. In step 260, respective BAC handicaps are determined for each player 110, 111, 112 and/or 113 for a hole to be played, such as one of the hole 150 based on such player's player-hole index for the hole to be played, and the received player BAC data. An exemplary method for determining the player-hole information is provided with respect to FIG. 6. Then, in step 270, the determined respective BAC handicaps for each player 110, 111, 112 and 113 for the hole 150 to be played is then transmitted by the computer server 130 to the user device 105. The BAC handicap includes information of any extra strokes to be awarded to each respective player 110, 111, 112 and 113 for playing the hole 150 based on both such player's skill level and level of intoxication.

Next, in step 280, if the golf round is not over, then the method reverts to step 250 for determination of the players BAC handicaps for the next hole, e.g., hole 155, of the golf course. The steps 250 through 280 are repeated for each hole of the golf course, until in step 280, it is determined that the golf round is over, then the method 200 ends.

FIG. 3 depicts a flow diagram of an exemplary alternative method 300 that may be executed on the computer server 130 of FIG. 1 for adjusting handicaps of golf players based on the player's BAC level. The method 300 may be performed for one or more of players 110, 111, 112 and 113, but for ease of understanding, the method will be described with regard to only player 110. It should be readily understood that the described method 300 with regard to player 110 during a golf round, could be repeated for the additional players 111, 112 and 113 during such golf round.

The method 300 begins with step 305 where the player handicap information is obtained for player 110, for example, from the GHIN as indicated by reference number 310 and described with regard to FIG. 2, or provided by the user device 105 or from some other source. Such player handicap information may be in the form of an index as provided by GHIN or some other form, and may be determined recent golf outing scores of the player 110 as indicated by reference 317. The corresponding resulting player handicap information is then represented by reference number 315.

Next, in step 320, the golf course information, such as for golf course 120, is obtained, such as by the player 110 selecting the golf course in an executed app or other software on the user device 105 configured to enable the player 110 to select the golf course, and then communicate with an internet-accessible computer server, such as computer servicer 130, or computer servers 140*a* and 140*b* to obtain such golf course information which is then loaded into the user device 105 in step 325.

A particular tee box from which player 110 will hit his golf ball from is then selected or is otherwise determined in step 330, if the selected golf course offers more than one tee box for any hole of such golf course. Based on the entered tee box and received or determined player handicap information, the method 300 in step 335 then determines the handicap information in the form of an exemplary handicap index of the player 110.

Next, in step 340, the player-hole index for player 110 is determined based on the golf course information, the player handicap information and the type of golf game to be played is then selected or entered in step 345. Next, the BAC data indicating the BAC level for player 110 is obtained or determined in step 350. Thereafter, in step 355, the BAC handicap information for player 110 is determined for the hole to be played based on such player's player-hole index for that hole, and the received player BAC data. An exemplary method for determining the player-hole information is provided with respect to FIG. 6. Lastly, in step 360 of FIG. 3, the player 110 tees off for the hole to be played. Then, steps 350 through 360 may be repeated for the player 110 for each hole or selected holes to be played on the golf course.

Figure 4:
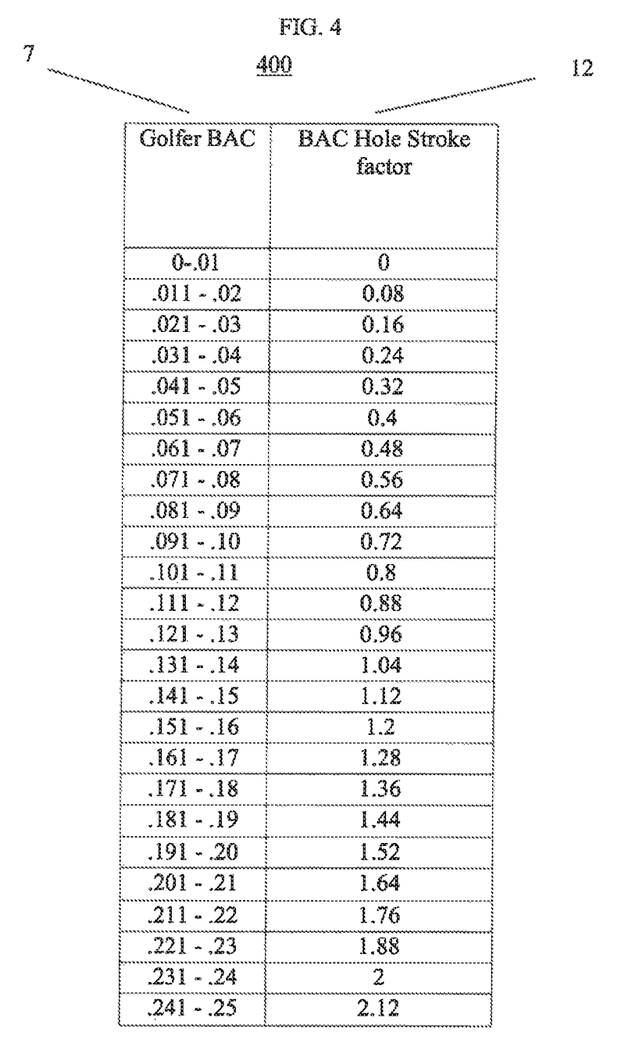
FIG. 4 depicts an exemplary conversion table of golfer BAC levels to BAC hole stroke factors.

FIG. 4 depicts an exemplary table 400 that may be maintained in digital form by the computer server 130 for specifying a representative relationship between golfer BAC data in column 7 and BAC hole stroke factor in column 12, and suitable for use in providing the associated information used by methods 200 and 300 of FIGS. 2 and 3. The BAC hole stroke factor values in this table may be updated based on collected information concerning player BAC and performance statistics.

Figure 5:
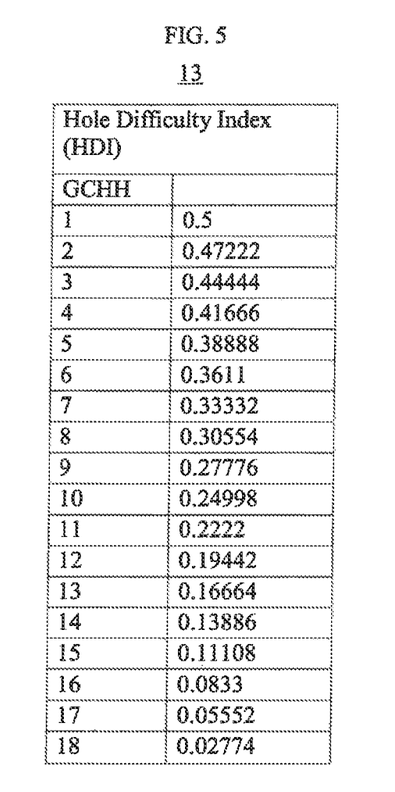
FIG. 5 depicts an exemplary sample hole difficult index for a hypothetical golf course.

FIG. 5 depicts an exemplary hole difficulty index (HDI) table 13 for each hole of a hypothetical golf course, such as golf course 120 of FIG. 1. The HDI table 13 may be maintained in digital form in any of computer servers 130, 140a, 140b, the user device 105 or some other network-accessible device. The indices of table 13 are indicative of the difficulty of a given hole at a golf course, such as par, distance to hole, hazards and other relevant factors, and is independent of and unrelated to a player's skill and level of intoxication. Suitable conventional HDI tables 13 are commonly available for numerous golf courses from commercial providers including, for example, the Golf Course Database (www.golf-course-database.com), the USGA's Course Rating and Slope Database™ (ncrdb.usga.org), the Swing app available from Swing Golf, Inc. (courses.swingbyswing.com), and the digital golf course maps from Golfbert Inc. (www.golfbert.com).

Figure 6:
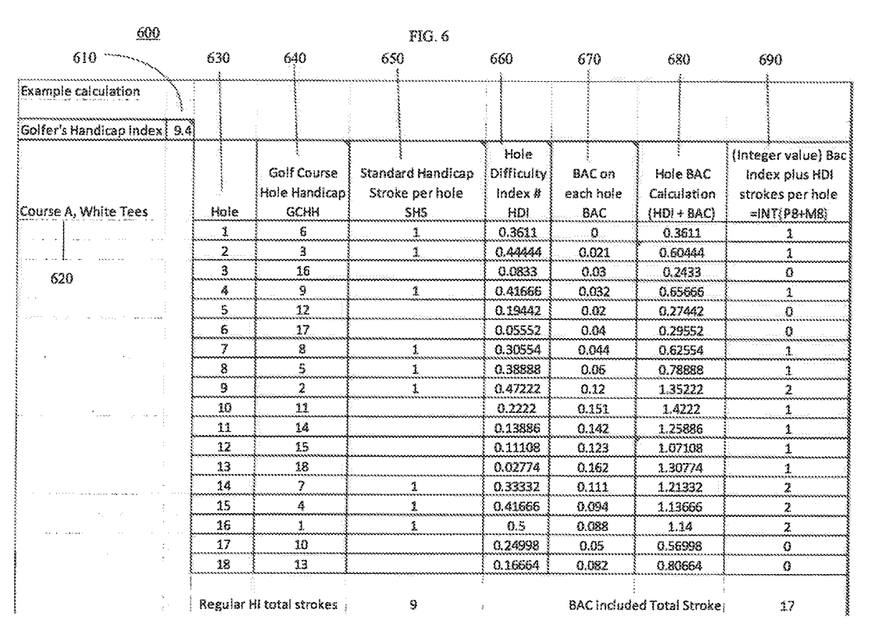
FIG. 6 depicts an exemplary table illustrating an algorithmic method for calculating the adjusted handicaps of players playing golf based on their BAC levels.

FIG. 6 depicts a table 600 of an exemplary algorithm for calculating the adjusted handicaps of players playing golf based on their level of intoxication at any particular hole of a golf course. The algorithm of table 600 is described with regard to the following hypothetical example for ease of understanding.

The particular golfer's handicap index of a 9.4 is provided at 610. This index is based on, for example, a standard handicap system, which will provide such golfer with one extra stroke for the nine most difficult holes of the hypothetical golf course and the tee box being played identified at table location 620. The hypothetical golf course has 18 holes as noted by column 630.

Column 640 provides a golf course hole handicap (GCHH) as values determined based on the difficulty of the hypothetical golf course, and are typically available from commercial providers for a large number of golf courses. The values in column 640 represent the difficulty of the corresponding holes identified in column 630, ranked from 1 to 18 based on difficulty, with the value 1 being the most difficult hole, which corresponds to hole 16. Based on the GCHH values, a standing handicap stroke per hole (SHS), represented in column 650, is assigned to each hole with the player's representative handicap index of 9.4, resulting in such player 1 being provided with one additional stroke on each of the nine most difficult holes, i.e., holes 1, 2, 4, 7, 8, 9, 14, 15 and 16.

HDI values are provided in column 660 that respectively correspond to the holes listed in column 630. The HDI values may be obtained in the manner described with regard to FIG. 5. A BAC level for the player may be obtained as described above with regard to FIGS. 1-3, and is provided in column 670 for a representative round of golf played on the course 620.

Column 680 includes hole-BAC level values that are the result of respective exemplary calculations, such as by method 200 of FIG. 2, performed prior to the player's tee off at each hole, but listed for the entire round of 18 holes of the hypothetical golf course for ease of illustration. The depicted hole-BAC level values in column 680 are based on the addition of (a) the HDI values for the respective holes of column 630 and (b) the BAC hole stroke factors, listed in FIG. 4, column 12, for the BAC values at each corresponding hole-BAC level listed in column 680.

Column 690 lists the resulting handicap value as the integer portion of the result of the addition of the respective SHS values of column 650 and hole-BAC values of column 680 for each of the 18 holes.

In the representative example of table 600, the player was provided with a total of 8 additional strokes due to the player's changing level of intoxication through the round of golf. The 8 additional strokes are in addition to the player's total SHS of 9 strokes, thus providing 17 total additional strokes as the total handicap.

It is to be understood that the invention is not limited to the particular embodiments of the invention described above, as variations of the particular embodiments may be made and still fall within the scope of the appended claims.

For example, it is to be understood that a variety of alternative possible calculations may be used to determine BAC handicap for a player per hole of a golf course based on the players difficulty in the playing the holes of such golf course, and the player's detected or estimated level of BAC at each hole or certain holes of such golf course, which are all intended to fall within the scope of the appended claims. Also, the computer sever may also dynamically collect information concerning player BAC and performance statistics for analysis confirm and/or revise the BAC handicapping calculation to be as generally accurate as practicable.

Also, a single user device and single breathalyzer was used in the above descriptions for ease of explanation purposes only. It is to be understood that more than one user device and breathalyzer may be used for a round of golf by a plurality of players including, for example, each player using her/his own user device (in communication with the remote computer server) and breathalyzer for the same round of golf.

Further, although the present invention was described with a computer server performing the BAC handicapping calculation, it is readily understood that such calculation may be performed by the user device 105, or any other computing device accessible to the golfers during a round of golf. Additionally, the methods herein may be adapted for use with other sports such as bowling or disc golf.

What is claimed is:

1. A computer server-implemented method for adjusting handicaps of players playing golf based on their level of intoxication, the method comprising the steps of:
   a. receiving handicap information of at least one player over a data network;
   b. receiving over the data network information associated with a golf course that the at least one player will play, the golf course information including levels of difficulty of playing respective holes of a plurality of holes of the golf course over the data network;
   c. determine player-hole information for each player of the at least one player based on the golf course information, the player handicap information for each player, and type of golf game to be played;
   d. receiving player-hole information over the data network from a user device associated with each player, said player-hole information including an identifier indicative of a hole to be played of the plurality of holes and player blood alcohol concentration ("BAC") data, wherein the player BAC data is indicative of the blood alcohol concentration for each player immediately prior to playing the hole to be played by the at least one player;
   e. for each respective player, determining a BAC handicap for the hole to be played based on such player's player-hole index for the hole to be played, and the received player BAC data; and
   f. transmitting to the user device the BAC handicap for each player for the hole to be played, wherein the BAC handicap includes an indication of any award of extra strokes to one of the players for a hole to be played based on both such player's skill level and level of intoxication.

2. The method of claim 1 wherein the player BAC data is determined based on at least one of a BAC detector or an entry into the user device the type and quantity of one or more alcoholic beverages consumed be the player.

3. The method of claim 1, wherein the BAC detector transmits detected player BAC data to the user device.

4. The method of claim 3 wherein the detector is a breathalyzer in at least one of a wired or wireless communication with the user device.

5. The method of claim 1, wherein the user device is a mobile device.

6. The method of claim 1, wherein the determining of the BAC handicap is based on at least one of an algorithm and a lookup table.

7. The method of claim 1, wherein at least one of the received information associated with a golf course, and the received identifier indicative of a hole to be played is provided by the user device.

8. The method of claim 7, wherein the user device basis its determination of the information associated with a golf course, and/or the identifier indicative of a hole to be played based on detected global positioning system (GPS) information.

9. The method of claim 7, wherein the step of determining the BAC handicap is based on predetermined hole BAC stroke factors corresponding to BAC data.

10. The method of claim 9, wherein the step of determining the BAC handicap for a hole to be played is based on the hole BAC stroke factors and a predetermined hole difficulty index.

* * * * *